United States Patent
Stephens et al.

(10) Patent No.: US 7,342,113 B2
(45) Date of Patent: Mar. 11, 2008

(54) COLORANT COMPOSITIONS

(75) Inventors: Eric B. Stephens, Spartanburg, SC (US); Pat Moore, Pacolet, SC (US)

(73) Assignee: Milliken & Company, Spartanburg, SC (US)

( * ) Notice: Subject to any disclaimer, the term of this patent is extended or adjusted under 35 U.S.C. 154(b) by 237 days.

(21) Appl. No.: 10/991,655

(22) Filed: Nov. 18, 2004

(65) Prior Publication Data

US 2006/0105927 A1    May 18, 2006

(51) Int. Cl.
*C07D 413/02* (2006.01)

(52) U.S. Cl. .................................................. 546/165

(58) Field of Classification Search ................ 546/165
See application file for complete search history.

(56) References Cited

U.S. PATENT DOCUMENTS

| | | | | |
|---|---|---|---|---|
| 3,927,044 | A | 12/1975 | Foster et al. | 260/394 |
| 4,113,721 | A | 9/1978 | Hauser et al. | 260/178 |
| 4,141,684 | A | 2/1979 | Kuhn | 8/39 R |
| 4,284,729 | A | 8/1981 | Cross et al. | 521/158 |
| 4,595,536 | A | 6/1986 | Hung et al. | 260/394 |
| 4,632,783 | A | 12/1986 | Hung et al. | 260/394 |
| 4,871,371 | A | 10/1989 | Harris | 8/403 |
| 5,362,612 | A * | 11/1994 | Kiekens et al. | 430/520 |
| 5,474,578 | A | 12/1995 | Chan et al. | 8/431 |
| 5,591,833 | A | 1/1997 | Hines et al. | 534/607 |
| 6,342,618 | B2 | 1/2002 | Harris | 552/101 |
| 6,395,797 | B2 | 5/2002 | Ragsdale et al. | 521/130 |
| 6,764,541 | B1 | 7/2004 | Banning et al. | 106/31.29 |
| 7,094,812 | B2 * | 8/2006 | Banning et al. | 523/160 |
| 2004/0143910 | A1 | 7/2004 | Said et al. | 8/405 |
| 2004/0214918 | A1 | 10/2004 | Banning et al. | 523/160 |

OTHER PUBLICATIONS

The Chemistry of Synthetic Dyes vol. IV by Academic Press—1971.
Triarylemethane Dyes Among the 2,2,4-Trimethylhydroquinolines Khimiya I khimicheskaya tekhnologiya, 1999, vol. 42, No. 4, pp. 83-87.
Concurrently filed "Colorant Compositions", Filed Nov. 18, 2004; Stephens et. Al., Milliken Case No. 5825.
Developments in the Chemistry and Technology of Organic Dyes, J. Griffiths, Published 1984.

* cited by examiner

*Primary Examiner*—D. Margaret Seaman
*Assistant Examiner*—Nizal S. Chandrakumar
(74) *Attorney, Agent, or Firm*—Terry T. Moyer; Brenda D. Wentz

(57) ABSTRACT

Colorant compositions are useful for a wide variety of product applications. For example, colorants are used in tinting of polymers, providing colors to aqueous solution(s), and affording color to solid or semi-solid products such as detergents. Disclosed herein are colorant compositions having a triphenylmethane ("TPM") structure having improved stability to alkaline conditions. Thus, the colorant compositions resist decolorization, even at relatively high pH levels.

4 Claims, No Drawings

COLORANT COMPOSITIONS

FIELD OF THE INVENTION

This invention relates to surprisingly effective triphenylmethane colorant compositions, which exhibit low color degradation in alkaline media.

BACKGROUND OF THE INVENTION

Colorant compositions are useful for a wide variety of product applications. For example, colorants are used for tinting of polymers, providing colors to aqueous solution(s), and affording color to solid or semi-solid products such as detergents. Crayons, ink compositions, toilet bowl colorants, plastics, soaps, and many other products are colored using triphenylamine-based colorant compositions.

Triphenylmethane ("TPM") colorants consist of three aromatic rings linked by a central carbon atom. TPM colorants can be prepared by first condensing an aromatic aldehyde with two equivalents of an aromatic amine (which will hereafter be referred to as the "coupler" or "coupling component") in the presence of an acid such as sulfuric acid, phosphoric acid, or muriatic acid. After condensation, the uncolored intermediate is oxidized using a variety of oxidizing agents (hydrogen peroxide, lead oxide, chromium oxide) to afford the TPM colorant. Variations in the substitution patterns on either the aldehyde or the coupler molecules can change slightly the wavelength of light absorbed, thus providing a different color to the colorant species. The substitution of groups in this manner is highly unpredictable. A large amount of effort may be expended to find the right molecular combination to provide the most appropriate color shade for a given application.

One problem with TPM colorants is inadvertent or undesirable discoloration. This may occur if an undesirable chemical reaction occurs to the colorant molecular species. In the case of TPM based colorants, nucleophilic groups such as OH— or certain basic amine groups may react with and undesirably decolorize or shift the shade of such colorants. It is known that at elevated pH levels, TPM based colorants are subject to hydroxyl (OH—) attack. These reactions may undesirably decolorize or change the shade of the colorant. Thus, it would be highly desirable to develop compositions, methods, or techniques that could be used for affording color in such product applications while providing a high level of stability in alkaline environments as well. This ensures that adequate color remains, even under alkaline conditions.

Discoloration of TPM colorants and or dyes has been addressed in a number of patents, which are discussed below.

In the "Ragsdale" patent (U.S. Pat. No. 6,395,797), organic cyclic ester additives were formulated with TPM colorants to reduce color degradation in polyurethane foam systems caused by certain tertiary amine catalyst.

In Harris (U.S. Pat. No. 6,342,618), TPM colorants containing sterically hindered fugitive amine counterions were disclosed for improving stability of such colorants in inks. The colorants disclosed are triphenylmethane polymeric colorants which are capped with a cyclic anhydride and the preferred sterically hindered amine counter ions are those based on low molecular weight fugitive tertiary amines, such as N,N-dimethylethanolamine.

U.S. Pat. No. 3,927,044 (Foster et al.) discloses alkaline stable fugitive tints prepared using aromatic aldehydes containing an electron-withdrawing group (X) in the ortho-position. These fugitive tints are prepared with highly ethoxylated aromatic amines. The tints are said to exhibit improved lightfastness and provide some degree of alkaline stability.

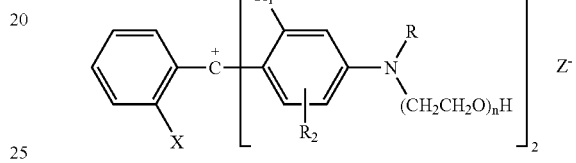

Stability is defined in this patent disclosure as the ability to retain color in an alkaline solution at a pH level of 11. The X in the structure represents the electron-withdrawing group in the ortho position and may include halogen, nitro, or sulfonyl radicals.

United States Patent Publication No. 2004/0143910 A1 discloses the use of certain triphenylmethane dyes as hair colorants, which are resistant to decolorization in alkaline bleach medium. This patent teaches that TPM dyes containing deactivating (electron withdrawing) or weakly activating groups substituted at the ortho- and/or para-positions relative to the central methane carbon and/or auxochrome groups (located on or attached to the aromatic rings of the TPM) have enhanced survival in alkaline bleach medium. As more and more groups are added to the rings, stability increases proportionally, so that dyes with the most substituents on all three aromatic rings are the most stable. These deactivating and protective groups may be nitro, halogen, cyano, carboxyl, sulfonic, alkyl, or aromatic groups, but not amino, hydroxy, alkoxy or alkylamide groups. In this patent auxochromes are defined as weakly basic groups such as hydroxy or amino groups. If the auxochrome is an amino group, it may be a primary amino group (—NH$_2$), a secondary amino group (—NHR$_1$), or a tertiary amino group (—NR$_2$) where R$_1$ and R$_2$ may be identical or different, and either may be alkyl, alkoxy, carboxy, cyano, alkyl cyano, halogen, phenyl, or naphthyl substituent.

A reduction in the rate of hydrolysis for TPMs containing methyl groups in the ortho substituents is also noted in Volumn IV of Venkataraman's series The Chemistry of Synthetic Dyes.

U.S. Pat. No. 4,595,536 (Hung et al) discloses TPM dyes of the structure shown below.

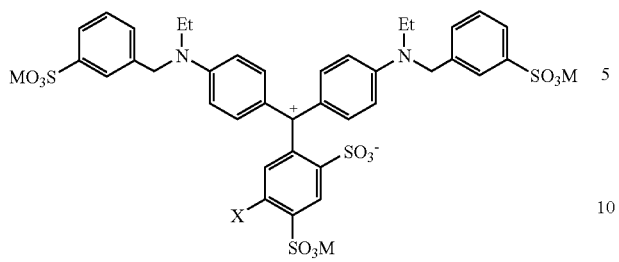

These dyes are reported to be resistant or stable enough to sanitizing agents, which produce hypochlorite in aqueous solutions. They may be used in automatic toilet bowl sanitizers. In this patent X represents hydrogen or hydroxy. M represents an alkali metal cation, an ammonium ion, or an alkaline earth metal cation.

An additional patent by Hung et al, U.S. Pat. No. 4,632,783 discloses TPM dyes of the structure shown below.

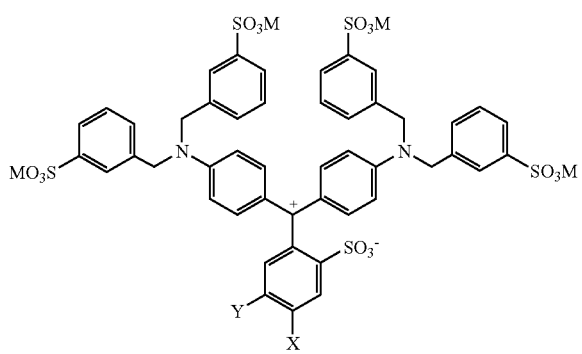

These dyes are also reported to be resistant or stable enough to sanitizing agents, which produce hypochlorite in aqueous solutions, that they can be used in automatic toilet bowl sanitizers. In this patent X represents hydrogen or the group SO3M. Y represents hydrogen or hydroxy. M represents an alkali metal cation, an ammonium cation, or an alkaline earth metal cation.

United States Patent No. 2004/0214918 A1 (Banning et al.) is directed to colorant compositions having aromatic ring structures with an attached nitrogen, in which the nitrogen is substituted with an R group, and also with an alkylene oxide containing structure. The R group may be alkyl, aryl, arylalkyl or an alkylaryl group. Further, the R group may be joined to the phenyl moiety to form a bicylic structure. The overall triphenyl-based structure proposed in this patent contains one alkylene oxide chain $(C_nH_{2n}O)_xH$ attached to the nitrogen. This alkylene oxide chain is derived from its presence on the aromatic aldehyde that is reacted two other phenyls to form the triphenyl-based structure. The non-ring based carbon of the aromatic aldehyde group forms the central carbon of the triphenylamine-based structure that is formed.

Shikhaliev et al (Khimiya I Khimicheskaya Tekhnologiya, 1999, Vol. 42, No. 4, pp 83-87) reported the preparation and spectral properties of the following TPM dyes of the structure shown below where $R_1$ is H or $NMe_2$ and R is H or Me.

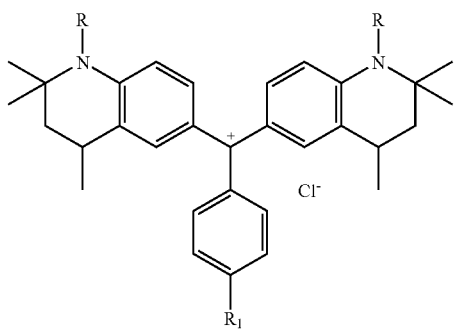

U.S. Pat. No. 5,591,833 to Hines et al is directed to fugitive tint materials that are more easily removed from yarns without scouring the yarns. The Hines patent discloses colorants and compositions useful as fugitive or permanent colorants for a variety of substrates, and having one or more improved properties, such as: enhanced aqueous washability, reduced staining, compatibility with and non-extractability from thermoplastic resins, and reactivity with resins having reactive functionality.

The compositions disclosed in Examples 63, 64, and 65 of the Hines patent incorporate long chain ethylene oxide (EO) residues containing at least two glycidols (denoted "GL" in the patent) attached to nitrogen. Example 63 contains two "H-50 EO/2GL-" groups, while Examples 64 and 65 disclose two "H-10 EO/2GL-" and two "H-50EO/2GL-" groups, respectively, attached to separate nitrogens annexed to a triphenylmethane-based compound. Hines discloses using between 2 and 6 glycidol residues attached to a nucleophilic site.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention.

In the practice of the invention, novel chemical compositions and methods of applying such chemical compositions are provided. A triphenylmethane-based colorant is provided that is stable in alkaline detergent systems as well as polyurethane systems that employ basic catalysts. Thus, detergent compositions containing the novel chemical colorants are disclosed as well.

TPM based compositions of the invention increase steric hinderance in the vicinity of the nitrogen atom on the coupler by employing a coupler wherein the nitrogen atom of the aromatic amine is incorporated into a ring system as in tetrahydroquinoline, tetramethylquinoline, benzomorpholine, etc. By using a coupler wherein this nitrogen is incorporated into a ring system, the likelihood that the TPM colorant will undergo decolorization due to attack by a nucleophile (such as OH— or an amine) is reduced dramatically and the stability of the colorant is improved. This is an unexpected and significant discovery.

The nitrogen on the aromatic amine coupler is further substituted by an alkylene oxide residue of ethylene oxide, butylene oxide, propylene oxide, etc. or mixtures thereof.

The use of couplers or aldehydes which contain groups that increase the steric hindrance in and around the central carbon of the TPM based structure can also be employed in conjunction with the before mentioned coupling components which contain the aromatic amine nitrogen bound in a ring system. Such additional steric hindrance can improve the stability further but is not always necessary.

The use of aromatic aldehyde components containing para-substituted amines may also be incorporated into the TPM composition. This, in general, allows one to obtain more violet to red shades of blue. The amine on the aldehyde component is substituted with alkylene oxide residues consisting of either propylene oxide, butylene oxide, styrene oxide, t-butyl glycidyl ether, isopropyl glycidyl ether, isobutyl glycidyl ether, 2-ethylhexyl glycidyl ether, glycidyl hexadecyl ether, glycidyl methyl ether.

If an amine is present on the aromatic amine aldehyde, it may be incorporated into a heterocycle as in the case of the structure shown below.

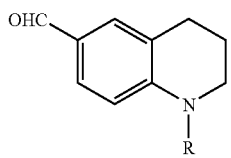

In this case the amine is additionally substituted with an R group which is an alkyl group or residues of styrene oxide, t-butyl glycidyl ether, isopropyl glycidyl ether, isobutyl glycidyl ether, 2-ethylhexyl glycidyl ether, glycidyl hexadecyl ether, glycidyl methyl ether or mixtures therof.

In one application of the invention, a composition as presented below may be provided:

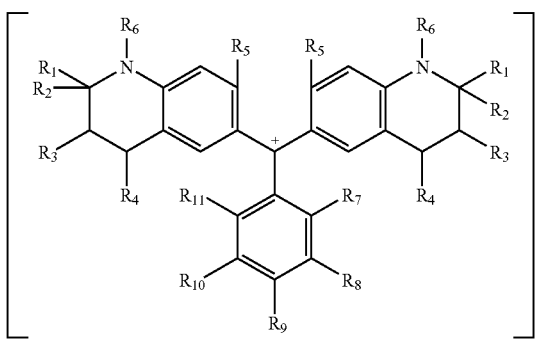

$R_1$, $R_2$, $R_3$, $R_4$, $R_5$, $R_7$, $R_8$, $R_{10}$ and $R_{11}$ each may be independently selected from the group consisting of: hydrogen, alkyl, alkoxy, $SO_3^-$, $SO_3Na$, $SO_3K$, sulfonamide, acetamide, nitro, and cyano;

$R_6$ comprises an alkylene oxide moiety;

$R_9$ may be selected from the group consisting of: H, $SO_3^-$, alkyl, $SO_3Na$, $SO_3K$, alkoxy, sulfonamide, cyano, acetamide, nitro, and nitrogen-bound alkylene oxide residues. A- comprises an anion.

In at least one application of the invention, at least two OH groups will reside upon the colorant molecule by terminating each $R_6$ group. Although many applications will provide more than two of such OH groups per molecule. The terminal OH groups may or may not be capped with acetate groups, or urethanes.

Furthermore, in other applications, a structure like that shown below (with two Oxygen atoms substituted on each side to form a heterocycle) may be provided, using essentially the same designations as provided above for the various substituted $R_x$ groups.

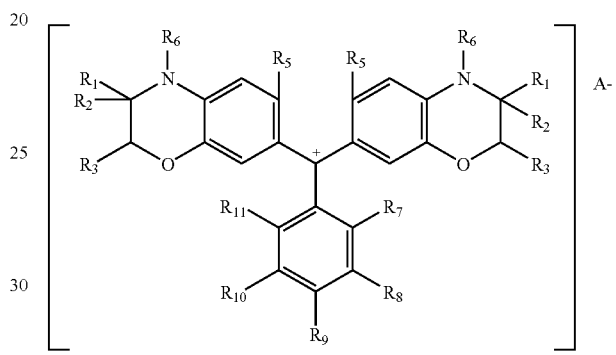

The colorant compositions as set forth above may be employed using at least two terminal —OH groups on said $R_6$ group(s). Further, at least one hydrogen may be employed on at least one of said terminal —OH groups using one of the following:

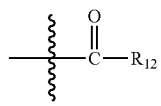

wherein $R_{12}$ is alkyl or

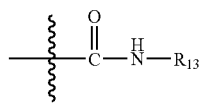

wherein $R_{13}$ is alkyl or aryl

Synthesis of Colorant Compositions

The synthesis of the inventive colorant compositions may be by several methods, described below. The invention and the scope of the claims are not limited to any particular method of making the composition, and these are representative examples of synthesis methods.

The coupling components wherein the aromatic amine nitrogen is contained within a ring system are prepared as follows.

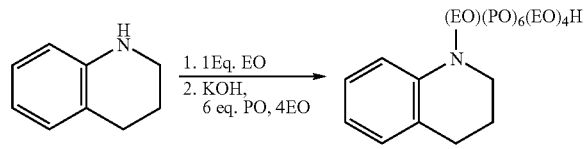

Tetrahydroquinoline 1EO 6PO 4EO is prepared in the following manner. Three hundred twenty grams of 1,2,3,4 tetrahydroquinoline was placed in a 1-gallon stainless steel pressure reactor equipped with an agitator, gas inlet tube, and vent. After purging with nitrogen, the reactor and contents were heated to 250 F. Ethylene oxide was added through the inlet tube until 1 equivalent or 109 g was consumed. After post reacting for 30 minutes, then subjected to vacuum for 15 minutes. Potassium hydroxide flake (15 g) was then added to the reactor. The reactor was heated to 200 F and subjected to vacuum for 15 minutes. Propylene oxide was then added into the reactor until 6 equivalents or 836 g were consumed. The reaction was post reacted for 30 minutes then subjected to vacuum for 15 minutes. Ethylene oxide was added into the reactor until 423 g were consumed. The reaction was post cooked for 30 minutes, then stripped for 15 minutes. The reaction was then cooled to ambient temperature to give tetrahydroquinoline 1EO 6PO 4EO as a straw colored liquid.

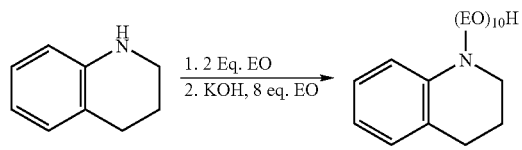

Tetrahydroquinoline 10 EO. Four hundred twenty-five grams of 1,2,3,4 tetrahydroquinoline was placed in a 1 gallon stainless steel pressure reactor equipped with an agitator, gas inlet tube, and vent. After purging with nitrogen, the reactor and contents were heated to 250 F. Ethylene oxide was added through the inlet tube until 1 equivalent or 280 g was consumed. After post reacting for 30 minutes, the mixture was subjected to vacuum for 15 minutes. Potassium hydroxide flake (7 g) was then added to the reactor. The reactor was heated to 200 F and subjected to vacuum for 15 minutes. Ethylene oxide was then added into the reactor until 8 equivalents or 1125 g were consumed. The reaction was post reacted for 30 minutes then cooled to ambient temperature to give tetrahydroquinoline 10 EO as an amber colored liquid.

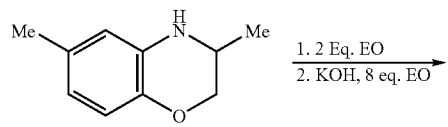

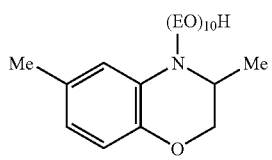

A hindered alkoxylated aromatic amine coupler can be prepared using 3,6-dimethyl-benzomorpholine and the procedure described above with the exception that 520.8 g of the 3,6-dimethylbenzomorpholine be used in place of the 425 g of tetrahydroquinoline.

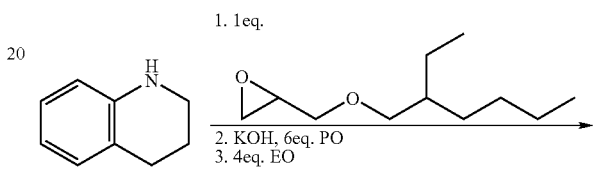

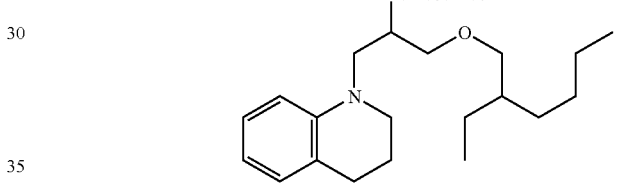

Tetrahydroquinoline 1 (2-ethylhexyl glycidol ether) 6PO 4EO. To a clean, dry 1000 mL 3-neck flask equipped with an agitator, thermometer, reflux condenser, and $N_2$ inlet was added tetrahydro-quinoline (95 g). The tetrahydroquinoline was heated to 120 C and 2ethylexyl glycidol ether (162.3 g) was dripped in. After the addition, the reaction mixture was post cooked for 2 additional hours at 115 and 130 C. The product was allowed to cool to ambient temperature to give the product tetrahydroquinoline 1 (2-ethylhexyl glycidol ether) 6PO 4EO as a clear oil.

Three hundred seventy five grams of tetrahydroquinoline 1(2-ethylhexyl glycidol ether) 6PO 4EO and 2 grams of potassium hydroxide were added to a 1 gallon stainless steel pressure reactor equipped with an agitator, gas inlet tube, and vent. After purging with nitrogen, the reactor and contents were heated to 200 F. Vacuum was applied for 15 minutes. The contents of the reactor were then heated to 250 F and propylene oxide was added into the reactor until 6 equivalents or 407 g were consumed. The reaction was post reacted for 30 minutes then subjected to vacuum for 15 minutes. Ethylene oxide was then added at 250 F until 4 equivalents or 207 g was consumed. The reaction was post reacted for 30 minutes then subjected to vacuum for 15 minutes. The reaction was then cooled to ambient temperature to give an tan colored liquid.

EXAMPLE 1

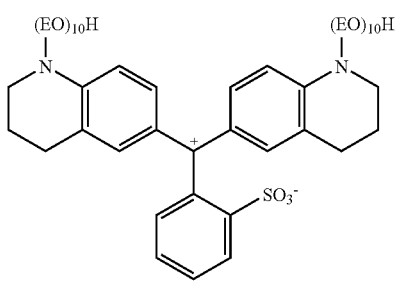

To a 500 mL 3-neck round bottom flask equipped with a condenser, thermometer and a $N_2$ inlet was added 93% sulfuric acid (6.0 g), ortho-formylbenzene sulfonic acid sodium salt (11.5 g), urea (0.55 g), and tetrahydroquinoline 10EO (65.0 g). The ensuing reaction was stirred and heated to 85-95C for 3 hours under nitrogen. The reaction solution was then allowed to cool to 55-60 C and ammonium meta vanadate (0.44 g) was added. The ensuing reaction mixture was heated to 80-90C where a mixture of water (7.5 g) and 35% hydrogen peroxide (18.5 g) was slowly added. The mixture was then allowed to cool to ambient temperature where 200 g of additional water was added. The pH was adjusted to 5.5-6.5 with a 1:1 mixture of aqua ammonia and water to give an aqua green solution with a color value of 7.6 (measured with a Beckman DU 650 UV visible spectrophotometer; abs/g/L in Methanol) with a Max Abs of 645 nm.

EXAMPLE 2

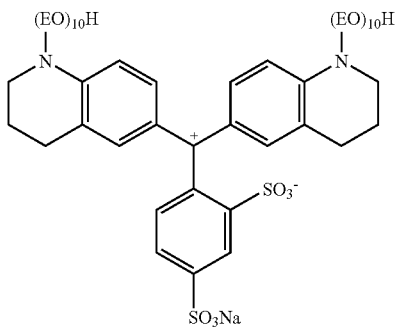

To a 3-neck 250 mL round bottom flask equipped with a condenser, thermometer and a $N_2$ inlet was added water (5.0 g), muriatic acid (7.0 g), 1,3-benzene-disulfonic acid-4-formyl-disodium salt (11.9 g), urea (0.3 g), and tetrahydroquinoline 10 EO (43.8 g). The ensuing reaction was stirred and heated to 80C for 3 hours under nitrogen. The reaction solution was then allowed to cool to 50 C and ammonium meta vanadate (0.55 g) was added. The ensuing reaction mixture was heated to 75-90C where a mixture of water (5.5 g) and 35% hydrogen peroxide (13.0 g) was slowly added. After addition of the peroxide water solution, 140 g of additional water was added and the pH was adjusted to 5.5-6.5 with a 1:1 mixture of aqua ammonia and water to give an aqua green solution with a color value of 9.4 (measured with a Beckman DU 650 UV visible spectrophotometer; abs/g/L in Methanol) with a Max Abs of 647 nm.

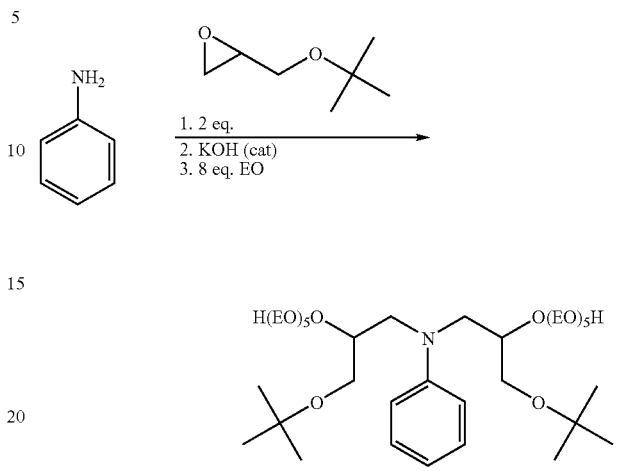

Preparation of Aniline 2TBGE 10 EO (where TBGE is tert-butyl glycidyl ether and EO is ethylene oxide. To a clean, dry 1 L 3-neck flask equipped with a stir rod, thermometer, condenser, and $N_2$ inlet was added at room temperature aniline (100 g)(available from Aldrich Chemical Co, Milwaukee, Wis.). Five drops of formic acid was then added and the contents stirred and heated to 120 C. At 120 C was added 300 g of tert-butylglycidyl ether (available from Aldrich Chemical Co, Milwaukee, Wis.). The reaction mixture was post-cooked at 150 C for 4 hours to give the Aniline 2TBGE intermediate as a straw colored wax.

Three hundred and thirty grams of the Aniline 2TBGE intermediate was placed in a 1-gallon stainless steel pressure reactor equipped with an agitator, gas inlet tube, and vent. Potassium hydroxide flake (1.5 g) was then added to the reactor. After purging with $N_2$, the reactor and contents were stripped at 200 C for 15 minutes. Ethylene oxide was then added into the reactor until 8 equivalents or 408 g were consumed. The reaction was post reacted for 30 minutes then cooled to ambient temperature to give an amber colored liquid.

The formylated adduct of Aniline 2TBGE 10 EO is prepared in the following multi-step process depicted in the scheme below.

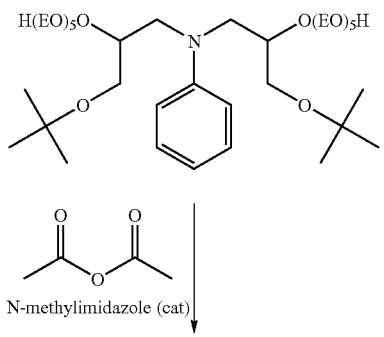

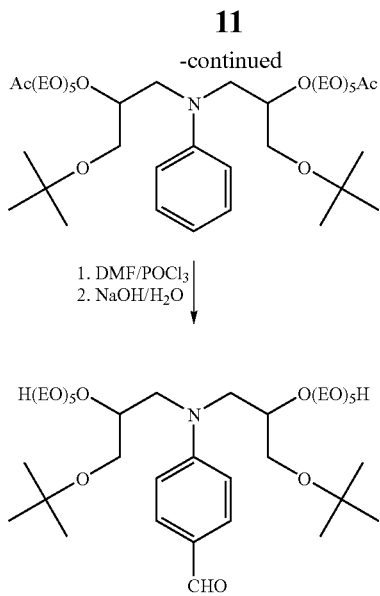

1. DMF/POCl₃
2. NaOH/H₂O

EXAMPLE 3

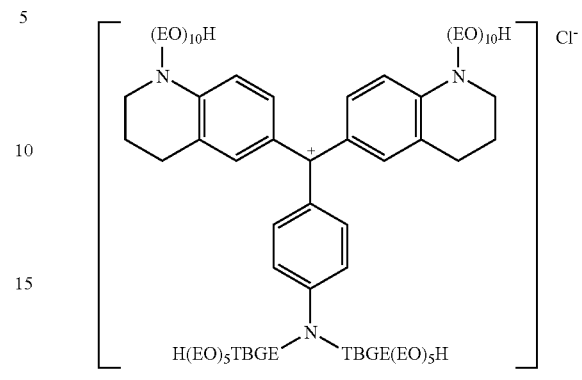

To a 3-neck 250 mL round bottom flask equipped with a condenser, thermometer and a N₂ inlet was added muriatic acid (7.0 g), formylated aniline 2TBGE 10EO (32.0 g, 75% solids), urea 0.3 g), and tetrahydroquinoline 10EO (43.8 g). The ensuing mixture was stirred and heated to 80C for 3 hours under a N₂ atmosphere. The reaction solution was then allowed to cool to 50 C and ammonium meta vanadate (0.55 g) was added. The ensuing reaction mixture was heated to 75-90C where a mixture of water (5.5 g) and 35% hydrogen peroxide (13.3 g) was slowly added. After addition of the peroxide water solution, 140 g of additional water was added and the mixture allowed to cool to 50C. The pH was adjusted to 5.5-6.5 with a 1:1 mixture of aqua ammonia and water to give a blue solution with a color value of 10.0 (measured with a Beckman DU 650 UV visible spectrophotometer; abs/g/L in Methanol) and a Max Abs of 611 nm.

Acetylation of Aniline 2TBGE 10 EO to give Aniline 2TBGE 10 EO diacetate. To a 1L 3-neck flask equipped with a thermometer, stirrer, condenser, and N₂ inlet was added Aniline 2TBGE 10 EO (400 g), acetic anhydride (129 g) and N-methylimidazole (1.5 g). The mixture was heated to 130 C for 3 hours under a N₂ atmosphere. The material was then stripped on a rotary evaporator to remove the acetic acid by-product to afford Aniline 2TBGE 10EO diacetate as a brown oil.

Formylation of Aniline 2TBGE 10 EO diacetate was accomplished in the following manner. To a clean, dry 500 mL 3-neck round bottom flask with a stirrer, thermometer, and N₂ inlet was added dimethylformamide (80 g). The flask was cooled to 5 C under a N₂ atmosphere and phosphorus oxychloride (60 g) was slowly added such that the temperature did not exceed 15 C. The ensuing solution was stirred 15 minutes at 5-15 C then slowly added to a 1L 3-neck flask containing Aniline 2TBGE 10 EO diacetate (250 g) at 5-30 C under a N₂ atmosphere with good mixing. The ensuing reaction mixture was heated to 75-85 C for 2 hours then allowed to cool to 40-50 C. The mixture was then slowly added to a stirring solution of water (393 g) and 50% sodium hydroxide (91 g) at 15-25 C. The mixture was then heated to 75 C and poured into a separatory funnel. The mixture was allowed to phase separate for 30 minutes. The bottom aqueous salt layer was removed. The top product layer was drained into a 1 L 3-neck flask equipped with a stir rod, thermometer, and condenser. Water (143 g), 50% sodium hydroxide (50 g) and 45% potassium hydroxide (6.8 g) were then added and the mixture heated to 95 C while stirring for 3 hours. The solution was then allowed to cool to 40-50 C and the pH adjusted to 7.5 with 93% sulfuric acid. The mixture was then heated to 75 C, poured into a separatory funnel and allowed to phase separate. The bottom aqueous salt layer was removed to give the formylated aniline 2TBGE 10 EO product as a brown solution of 75% solids with a color value of 28.4 (measured with a Beckman DU 650 UV visible spectrophotometer; abs/g/L in Methanol) and a Max Abs of 340 nm indicating the presence of the aldehydes functionality.

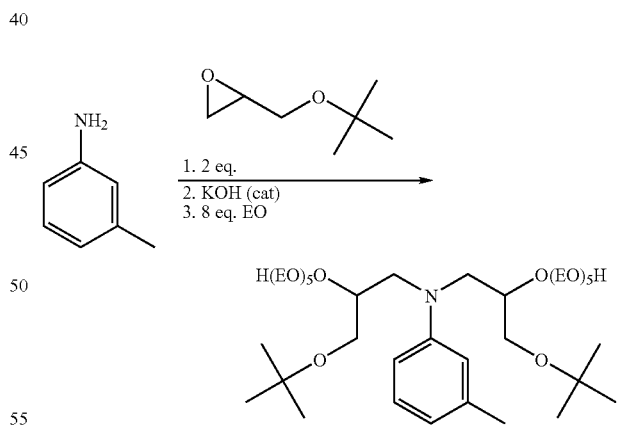

mToluidine 2TBGE 10 EO was prepared in the following manner. To a clean, dry 1 L 3-neck flask equipped with a stir rod, thermometer, condenser, and N₂ inlet was added at room temperature mToluidine (100 g)(available from Aldrich Chemical Co, Milwaukee, Wis.). Five drops of formic acid was then added and the contents stirred and heated to 120 C. At 120 C was added 290 g of tert-butylglycidyl ether (available from Aldrich Chemical Co, Milwaukee, Wis.).

The reaction mixture was post-cooked at 150 C for 4 hours to give the mToluidine 2TBGE intermediate as a straw colored wax.

Three hundred and thirty grams of the m-Toluidine 2TBGE intermediate was placed in a 1-gallon stainless steel pressure reactor equipped with an agitator, gas inlet tube, and vent. Potassium hydroxide flake (1.5 g) was then added to the reactor. After purging with $N_2$, the reactor and contents were stripped at 200 C for 15 minutes. Ethylene oxide was then added into the reactor until 8 equivalents or 396 g were consumed. The reaction was post reacted for 30 minutes then cooled to ambient temperature to give mToluidine 2TBGE 10 EO as an amber colored liquid.

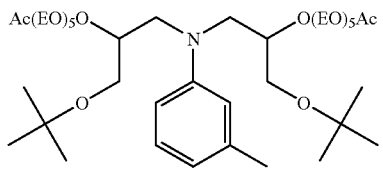

Acetylation of mToluidine 2TBGE 10 EO to give mToluidine 2TBGE 10EO diacetate. To a 1L 3-neck flask equipped with a thermometer, stirrer, condenser, and $N_2$ inlet was added m-Toluidine 2TBGE 10 EO (280 g), acetic anhydride (100 g) and N-methylimidazole (1.6 g). The mixture was heated to 130 C for 3 hours under a $N_2$ atmosphere. The material was then stripped on a rotary evaporator to remove the acetic acid by-product to afford mToluidine 2TBGE 10EO diacetate as a brown oil.

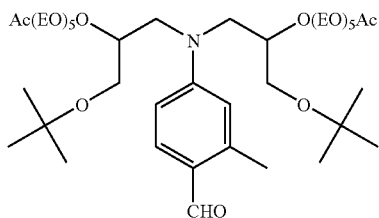

Formylation of mToluidine 2TBGE 10 EO diacetate. To a clean, dry 500 mL 3-neck round bottom flask with a stirrer, thermometer, and $N_2$ inlet was added dimethylformamide (109.4 g). The flask was cooled to 5 C under a $N_2$ atmosphere and phosphorus oxychloride (81.8 g) was slowly added such that the temperature did not exceed 15 C. The ensuing solution was stirred 15 minutes at 5-15 C then slowly added to a 1L 3-neck flask containing m-Toluidine 2TBGE 10 EO diacetate (300 g) and acetic anhydride (2.7 g) at 5-30 C under a $N_2$ atmosphere with good mixing. The ensuing reaction mixture was heated to 85-95 C for 2 hours then allowed to cool to 40-50 C. The mixture was then slowly added to a stirring solution of water (430 g) and 50% sodium hydroxide (249 g) at 15-25 C. The mixture was then heated to 75 C and poured into a separatory funnel. The mixture was allowed to phase separate for 30 minutes. The bottom aqueous salt layer was removed. The top product layer was drained into a 1 L 3-neck flask equipped with a stir rod, thermometer, and condenser. Water (101 g), 50% sodium hydroxide (64.3 g) and 45% potassium hydroxide (8.7 g) were then added and the mixture heated to 95 C while stirring for 3 hours. The solution was then allowed to cool to 40-50 C and the pH adjusted to 7.5 with 93% sulfuric acid. The mixture was then heated to 75 C, poured into a separatory funnel and allowed to phase separate. The bottom aqueous salt layer was removed to give the formylated mToluidine 2TBGE 10 EO product as a 75% solids brown solution of and a Max Abs of 340 nm.

EXAMPLE 4

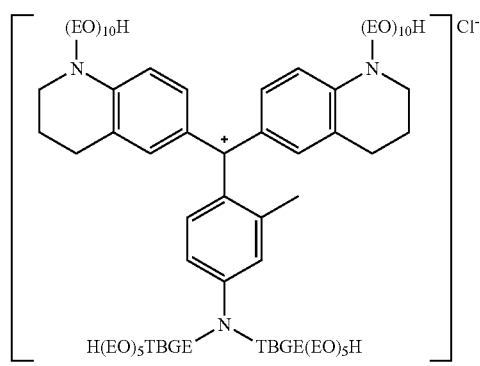

To a 3-neck 250 mL round bottom flask equipped with a condenser, thermometer and a $N_2$ inlet was added muriatic acid (8.3 g), formylated m-toluidine 2TBGE 10EO (22 g, 75% solids), urea (0.3 g), and tetrahydroquinoline 10EO (30.1 g). The ensuing mixture was stirred and heated to 80C for 3 hours under a nitrogen atmosphere. The reaction solution was then allowed to cool to 50 C and ammonium meta vanadate (0.33 g) was added. The ensuing reaction mixture was heated to 75-90C where a mixture of water (6.8 g) and 35% hydrogen peroxide (15.4 g) was slowly added. After addition of the peroxide water solution, 15 g of additional water was added and the mixture allowed to cool to 50C. The pH was adjusted to 5.5-6.5 with a 1:1 mixture of aqua ammonia and water to give an blue solution with a color value of 13.8 (measured with a Beckman DU 650 UV visible spectrophotometer; abs/g/L in Methanol) with a Max Abs of 621 nm.

The following examples are not considered the invention but were made as comparative examples for testing purposes.

COMPARATIVE EXAMPLE A

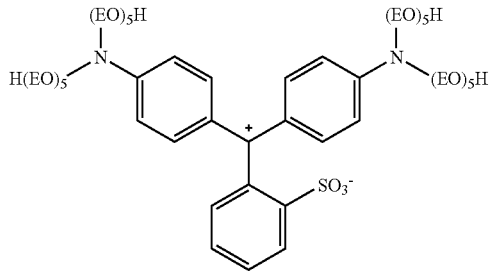

To a 4-neck 1000 mL round bottom flask equipped with a thermometer, condenser, stirrer and a N₂ inlet was added muriatic acid (36.5 g), water (4.8 g), ortho-formylbenzene sulfonic acid sodium salt (21.7 g), Aniline 10 EO (110.8 g), and urea (2.2 g). The ensuing mixture was heated to 95C for 3 hours under a N₂ atmosphere. The reaction solution was then allowed to cool to 75 C and ammonium meta-vanadate (0.14 g) was added. The ensuing reaction mixture was heated to 95C where a mixture of water (21 g) and 35% hydrogen peroxide (21 g) was slowly added. After addition of the peroxide water solution, the mixture was allowed to cool to ambient temperature. The pH was adjusted to 4.3 with 50% sodium hydroxide solution. Water (137 g) was then added to give a blue solution with a color value of 37 (measured with a Beckman DU650 UV visible spectrophotometer; abs/g/L in Methanol) and a Max Abs of 628 nm.

COMPARATIVE EXAMPLE B

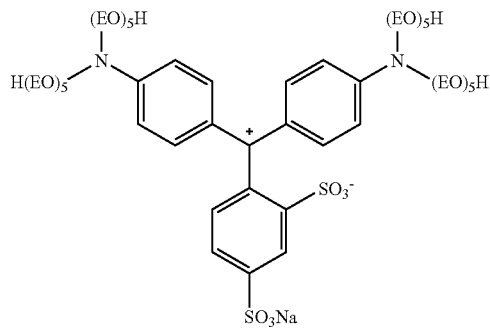

To a 4-neck 1000 mL round bottom flask equipped with a thermometer, condenser, stirrer and a N₂ inlet was added 93% sulfuric acid (9.3 g), 1,3-benzenedisulfonic acid-4-formyl-disodium salt (16.6 g), Aniline 10EO (57.0 g), and urea (0.3 g). The ensuing mixture was heated to 80C for 3 hours under a N₂ atmosphere. The reaction solution was then allowed to cool to ambient temperature and ammonium meta-vanadate (0.2 g) was added. The ensuing reaction mixture was heated to 75C where a mixture of water (8 g) and 35% hydrogen peroxide (18.5 g) was slowly added. After addition of the peroxide water solution, water (25 g) was added to the reaction mixture. The pH was adjusted to 5.9 with a 1/1 solution of aqua ammonia and water to give a blue solution with a color value of 21.6 (measured with a Beckman DU650 UV visible spectrophotometer; abs/g/L in Methanol) and a Max Abs of 632 nm.

COMPARATIVE EXAMPLE C

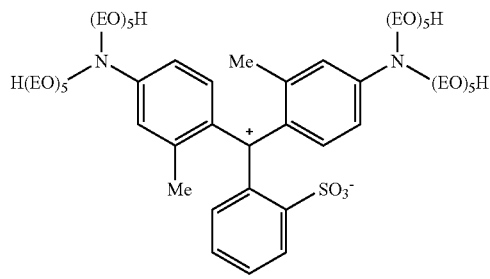

To a 3-neck 500 mL round bottom flask equipped with a thermometer and a N₂ inlet was added muriatic acid (10.3 g), water (22 g), ortho-formylbenzene sulfonic acid sodium salt (15.4), m-Toluidine 10EO (81.1 g), and urea (0.6 g). The ensuing mixture was heated to 95C for 3 hours under a N₂ atmosphere. The reaction solution was then allowed to cool to 75 C and ammonium meta-vanadate (0.4 g) was added. The ensuing reaction mixture was heated to 90C where a mixture of water (21 g) and 35% hydrogen peroxide (21 g) was slowly added. After addition of the peroxide water solution, the mixture was allowed to cool to ambient temperature. The pH was adjusted to 5.7 with a 1:1 mixture of aqua ammonia and water to give a green solution with a color value of 7.1 (measured with a Beckman DU 650 UV visible spectrophotometer; abs/g/L in Methanol) and a Max Abs of 648 nm.

COMPARATIVE EXAMPLE D

Xylene cyanol FF (Aldrich Chemical Co., Milwaukee, Wis.) will be used in stability test as comparative example E. The structure is below.

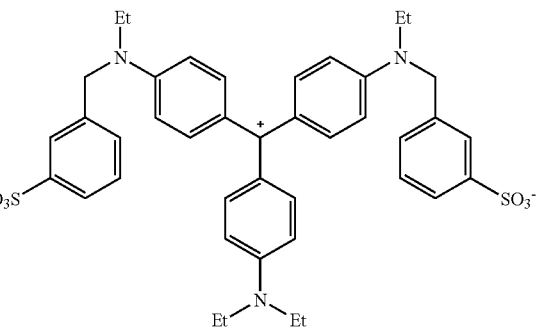

COMPARATIVE EXAMPLE E

Acid Violet 17 (Aldrich Chemical Co., Milwaukee, Wis.) will be used in stability test as comparative example E.

COMPARATIVE EXAMPLE F

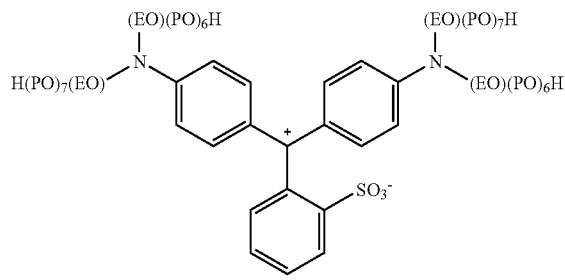

To a 3-neck 500 mL round bottom flask equipped with a thermometer and a nitrogen inlet was added 93% sulfuric acid (5.7 g), water (7.5 g), ortho-formylbenzene sulfonic acid sodium salt (11.5 g), Aniline 2EO 13PO (100 g), and urea (0.6 g). The ensuing mixture was heated to 95C for 3 hours under a nitrogen atmosphere. The reaction solution was then allowed to cool to ambient temperature and ammonium meta-vanadate (0.44 g) was added. The ensuing reaction mixture was heated to 95C where a mixture of water (7.5 g) and 35% hydrogen peroxide (18.5 g) was slowly added. After addition of the peroxide water solution, the solution was allowed to phase separate. A bottom aqueous layer was removed. To the product layer was added 200 g of water. The pH was adjusted to 7 with a 1:1 mixture of aqua ammonia and water. The mixture was then heated to 70 C and allowed to phase separate. The bottom product layer was removed and the wash procedure repeated. The final product layer was stripped via rotary evaporator to remove residual water to give a blue oil with a color value of 50 (measured with a Beckman DU 650 UV visible spectrophotometer; abs/g/L in Methanol) and a Max Abs of 628 nm in MeOH.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

The following solution stability test demonstrates the much improved stability of the TPM colorants of the present invention compared to other prior art TPM colorants.

TPM colorants were mixed equally with Liquitint® Red ST (available from Milliken Chemical). Since Liquitint® Red ST is stable at elevated pHs, it serves as a reference peak for determining the amount of TPM colorant lost during the test. 1% solutions of the colorant blends were then prepared by diluting the TPM/Red ST blends with DI Water. Using a DU 650 UV Vis spectrophotometer, the ratio of the Red ST maximium absorbance peak to the TPM maximum absorbance peak was measured and recorded for each blend as an initial reading. The 1% solutions were then mixed with equal amounts of pH 10 buffer solution (Available from VWR International, West Chester, Pa.) and placed in a 50 C oven for 16 hours.

After 16 hours at 50 C, the samples were allowed to cool to ambient temperature and the ratio of the Red ST maximum absorbance peak to the TPM maximum absorbance peak was measured and recorded for each blend as the final ratio. Using this value and the initial ratio, the amount or percentage of TPM lost during the test was determined. Table 1 below shows the results of the stability test.

TABLE 1

COLORANT STABILITY TEST IN AQUEOUS SOLUTION

| Example # | Aldehyde Component | Coupling Component | Red/TPM Peak Ratio Initial | Red/TPM Peak Ratio Final | % TPM Lost |
|---|---|---|---|---|---|
| Compare Example A | OFBSA | Aniline 10 EO | 0.598 | 1.043 | 42.7 |
| Example 1 | OFBSA | THQ 10 EO | 1.43 | 1.45 | 1.4 |
| Compare Example B | 1,3-disulf | Aniline 10 EO | 0.545 | 1.324 | 58.8 |
| Example 2 | 1,3-disulf | THQ 10 EO | 0.541 | 0.561 | 3.5 |

From the results in TABLE 1, it can be seen that the inventive colorants (Examples 1 & 2) showed a dramatic reduction in the amount of color lost in solution at a pH of 10 compared to the comparative TPM colorants, Examples A & B. These dramatic improvements are very unexpected.

Additional stability test were performed on powdered laundry detergents. In this test colorants were mixed with the detergent using the following procedure. Zeolite A (44 g) was added into a cup of a small food processor (Cuisineart Mini-Prep Plus). Three grams of color and three grams of water were then added. The components were then mixed for 5 minutes using the "grind" power setting on the food processor. Sodium sulfate (33.3 g) was then added to the mixture and the material was mixed for 5 minutes using the "grind" power setting on the food processor. The ensuing colored mixture was then mixed with Omo Laundry Detergent in a ratio of 1.25 g/48.75 g respectively. The ensuing material was mixed well.

The ensuing color/detergent mixtures were then measured on a GretagMacBeth Spectrophotometer to determine the initial reflectance. The samples were then placed in a 50 C oven for 3 weeks after which time they were removed and measured on the Gretag MacBeth Spectrophotometer to determine final reflectance. The % color loss was determined by comparing the initial reflectance measurements to the final measurements.

TABLE 2

COLORANT STABILITY ON LAUNDRY DETERGENTS

| Example # | Aldehyde Component | Coupling Component | % TPM Lost |
|---|---|---|---|
| Compare Example A | OFBSA | Aniline 10 EO | 26 |
| Compare Example C | OFBSA | MTol 10 EO | 41 |
| Compare Example D Xylene Cyanol FF | 1,3-benzene-disulfonic acid-4-formyl disodium salt | N-ethyl-ortho-toluidine | 80 |
| Comparative Example E Acid Violet 17 | N,N-diethyl-para-amino benzaldehyde | α-(N-ethylanilino)-m-toluenesulfonic acid | 100 |
| Example 1 | OFBSA | THQ 10 EO | <1 |
| Example 2 | 1,3-benzene-disulfonic acid-4- | THQ 10 EO | <1 |

TABLE 2-continued

COLORANT STABILITY ON LAUNDRY DETERGENTS

| Example # | Aldehyde Component | Coupling Component | % TPM Lost |
|---|---|---|---|
| | formyl disodium salt | | |
| Example 3 | PFA 2TBGE 10 EO | THQ 10 EO | <1 |
| Example 4 | PFT 2TBGE 10 EO | THQ 10 EO | <1 |

The results in TABLE 2 show that the inventive colorants (Examples 1-4) showed a dramatic reduction in the amount of color lost in laundry detergents compared to the comparative TPM colorants, Examples A, C, D, & E. These dramatic improvements are very unexpected.

In order to test the improved stability of the inventive colorants to basic amine catalyst in polyurethane foam, the following test was performed using the colorants described above. An inventive colorant was tested against a TPM colorant prepared using coupling components containing ethylene oxide residues attached directly to the nitrogen of the coupler.

In this test, the TPM colorants were mixed with other poly-(oxyalkylene) colorants which are stable to basic amine catalyst. This allows one to more easily see changes in the actual foam shade. This also provides a reference point from which to determine the actual percentage of colorant lost during the test. Black colorant blends were prepared by mixing equal amounts of Reactint® Red X64 and Reactint® Yellow X15 (available from Milliken Chemical, Spartanburg, S.C.) with comparative colorant F and inventive colorant 5.

In order to correct for varying color strengths, the colorants were all cut to a consistent color value of 25 (abs/g/L in Methanol) with a polyester polyol diluent (Fomrez 11-225.TM. from Witco) prior to mixing with Reactint® Red X64 and Reactint® Yellow X15 referenced above. This was accomplished as follows.

Standard polyurethane foams (to be used as reference foams) were prepared using the following procedure: Two parts of a colorant blend were added to 100 parts of ether triol (mw~3,000), which was mixed with 4.53 parts water, 1.0 part silicone surfactant, 0.15 parts stannous octoate catalyst (Dabco 33LV) and 0.60 parts triethylene diamine. Next, 58.8 parts toluene diisocyanate (80/20) was allowed to react at ambient conditions for approximately three minutes and allowed to cool. The foams were then cured in a microwave at 10% power for 10 minutes then in a 160 C oven for 3 minutes. A colored polyurethane foam having a density of 1.5 lbs./ft$^3$ was produced.

Test foams were made using the procedure described above except that the triethylamine diamine was replaced with either DABCO TL, DMEA, or ZF10. After the foams had cooled to room temperature, they were cut and an K/S spectral curve of the color of the center of the foam measured using a Hunter Color Computer. This spectra was compared to the K/S spectra from the center of the bun prepared using the same black colorant blend with triethylene diamine catalyst. By comparing the ratio of peak heights of the Blue peaks to that of the Red peaks in the foams for the standard catalyst (triethylene diamine) and the more basic amine catalyst, the % color loss can be determined. The results are shown in Table 3.

TABLE 3

COLORANT STABILITY TEST IN POLYURETHANE FOAM

| Example # | Aldehyde Component | Coupling Component | DMEA Catalist % Color Lost | ZF10 Catalist % Color Lost | DABCO TL Catalist % Color Lost |
|---|---|---|---|---|---|
| Comp. Ex. F | OFBSA | Aniline 2EO 13PO | 38 | 55 | 88 |
| Example 5 | OFBSA | THQ 2EHG6PO4EO | 2 | 10 | 52 |

From the results in TABLE 3, it can be seen that the inventive colorant 5 made using the tetrahydroquinoline based coupler, with the amine nitrogen contained in a heterocycle, showed a dramatic reduction in the amount of color lost in the presence of the highly basic amine catalyst compared to the comparative TPM colorant F wherein the amine nitrogen of the aromatic amine coupling component was not contained within a heterocycle but instead contained EO directly bound to the amine nitrogen of the coupler. The amount of improvement varies depending on the catalyst used.

The above examples and specification are intended and indeed serve as merely representative examples of the application of the invention. The invention is not strictly limited by such examples.

What is claimed is:

1. A colorant composition comprising:

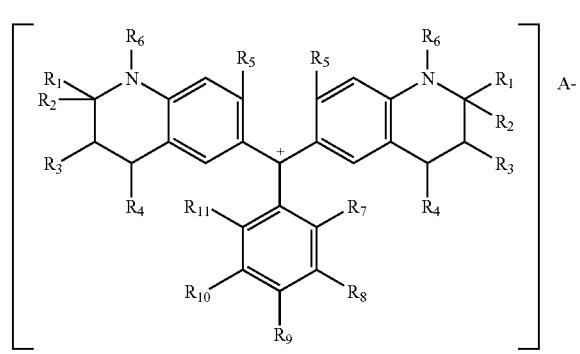

wherein $R_1$, $R_2$, $R_3$, $R_4$, $R_5$, $R_7$, $R_8$, $R_{10}$ and $R_{11}$ each are independently selected from the group consisting of: hydrogen, alkyl, alkoxy, $SO_3^-$, $SO_3Na$, $SO_3K$;

$R_6$ comprises an alkylene oxide moiety;

$R_9$ is selected from the group consisting of: hydrogen, $SO_3^-$, alkyl, $SO_3Na$, $SO_3K$, alkoxy, and a nitrogen-bound alkylene oxide moiety; and A— comprises an anion when said colorant composition does not contain $SO_3^-$.

2. The colorant composition of claim 1 wherein said $R_9$ comprises said nitrogen-bound alkylene oxide moiety, which further comprises a structure represented by:

$$N[(B)_y(C)_z H]_2$$

wherein

N is nitrogen;

H is hydrogen;

B represents an alkylene oxide residue, said alkylene oxide residue being selected from the group consisting of:

propylene oxide, butylene oxide, styrene oxide, t-butyl glycidyl ether, isopropyl glycidyl ether, isobutyl glycidyl ether, 2-ethylhexyl glycidyl ether, glycidyl hexadecyl ether, glycidyl methyl ether;

y is an integer between 1 and about 20; and

C represents an alkylene oxide residue selected from the group consisting of: ethylene oxide, propylene oxide, butylene oxide, styrene oxide, t-butyl glycidyl ether, isopropyl glycidyl ether, isobutyl glycidyl ether, 2-ethylhexyl glycidyl ether, glycidyl hexadecyl ether, and glycidyl methyl ether; and z represents an integer less than about 20.

3. The colorant composition of claim 1 comprising at least two terminal —OH groups, on said $R_6$ group(s).

4. The colorant composition of claim 3 wherein at least one hydrogen on at least one of said terminal —OH groups is replaced by one from the following group:

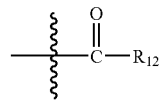

wherein $R_{12}$ is alkyl or

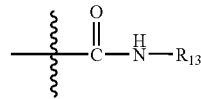

wherein $R_{13}$ is alkyl or aryl.

* * * * *